United States Patent

Stroot

[11] 4,045,825
[45] Sept. 6, 1977

[54] HUMERUS PROSTHESIS

[76] Inventor: Jerome H. Stroot, 2645 Ocean Ave., San Francisco, Calif. 94132

[21] Appl. No.: 653,277

[22] Filed: Jan. 28, 1976

[51] Int. Cl.$^2$ .................. A61F 1/24; A61F 1/02; A61F 1/04
[52] U.S. Cl. .................. 3/1.91; 128/92 C; 128/92 CA
[58] Field of Search .................. 3/1.9–1.913, 3/1; 128/92 C, 92 CA

[56] References Cited

U.S. PATENT DOCUMENTS

| | | | |
|---|---|---|---|
| 3,694,820 | 10/1972 | Scales et al. | 3/1.91 |
| 3,859,669 | 1/1975 | Shersher | 128/92 CA |

Primary Examiner—Ronald L. Frinks
Attorney, Agent, or Firm—Robert G. Slick

[57] ABSTRACT

A novel humerus element is provided which forms part of a total shoulder prosthesis. The novel prosthesis provides greater freedom of action and also provides a superior method of reattaching the tendons to the bone.

1 Claim, 4 Drawing Figures

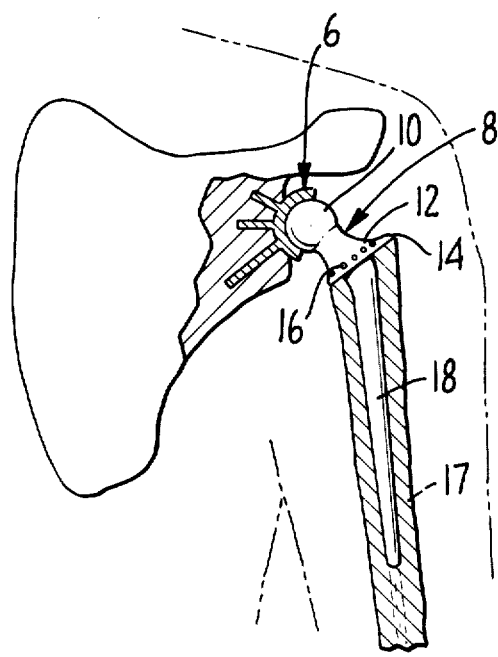
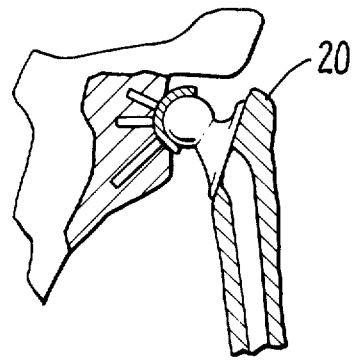
PRIOR ART
FIG. 2.
FIG. 1.
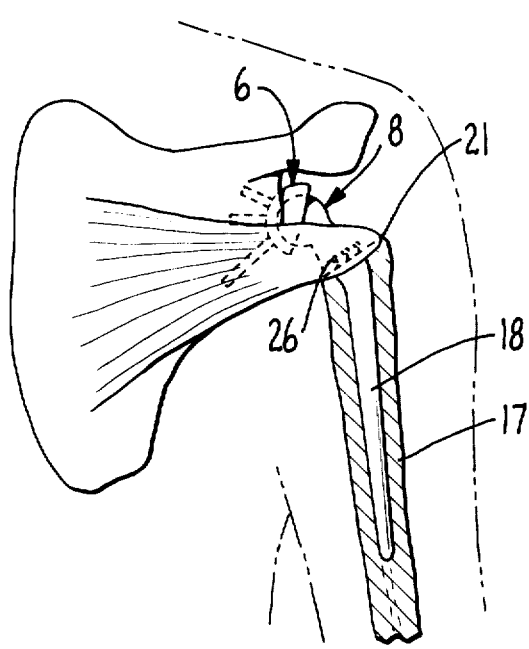
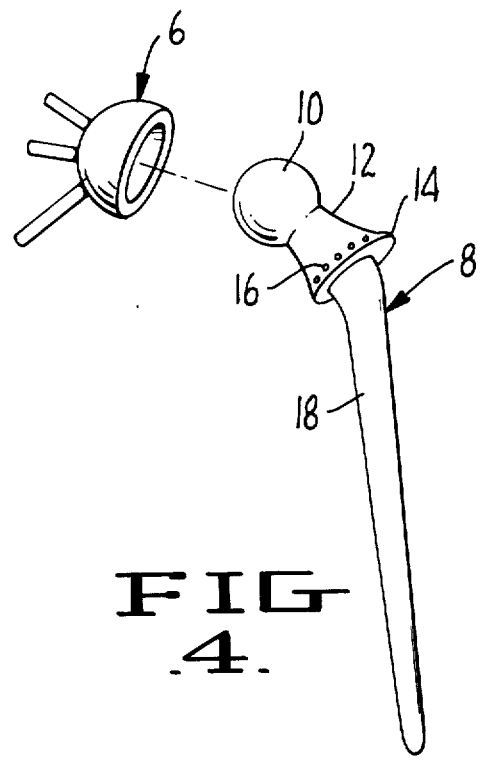
FIG. 4.
FIG. 3.

HUMERUS PROSTHESIS

SUMMARY OF THE INVENTION

One of the most successful shoulder replacements is that known as the Stanmore prosthesis covered by U.S. Pat. No. 3,694,820. This is a successful prosthesis and consists of a ball and socket joint with suitable means for attaching the two components to bone.

The present invention provides a novel humeral component for use in conjunction with such a prosthesis. The humeral component differs from the conventional Stanmore humeral component in that a shoulder is provided which has a series of holes therein through which sutures pass which expedites fixation of tendons to bone. The shoulder extends at substantially right angles to the center of curvature of the ball and the neck of the prosthesis is elongated. The Stanmore prosthesis was originally designed to preserve the rotator cuff (conjoined tendons consisting of the subscapularis in front, infraspinatus and teres minor muscles behind). In arthritis and similar conditions the rotator cuff frequently causes the tuberosity to impinge on the acromion, restricting movement. With the novel humerus element of the present invention the rotator cuff and the tuberosity are removed, allowing free movement of the shoulder.

The objects of the present invention are thus to provide an improved humeral component for a shoulder prosthesis which gives an increased freedom of action and which provides an efficient method of fastening the tendons to the bone. Furthermore, the novel humeral component described herein necessitates the removal of the tuberosities of the humerus (which oftentimes impedes abduction) which are left in place by the use of the standard Stanmore prosthesis. The holes in the shoulder of the prosthesis of the present invention are used for the passage of sutures to reattach the rotator cuff to bone.

BRIEF DESCRIPTION OF THE DRAWINGS

In the drawings forming part of this application:

FIG. 1 is an anterior view, partially in section, of a total shoulder prosthesis embodying the novel humeral component of the present invention.

FIG. 2 is a partial view, similar to FIG. 1, showing the Stanmore prosthesis of the prior art.

FIG. 3 is an anterior view showing the removal of the tuberosities of the humerus and the attachment of the rotator cuff to bone with sutures passing through holes in the prosthesis.

FIG. 4 is an exploded view showing a total shoulder prosthesis embodying the humeral component of the present invention.

DESCRIPTION OF THE PREFERRED EMBODIMENTS

The prosthesis of the present invention is designed to be used with a standard Stanmore socket joint, generally designated 6. Such sockets are well known to those skilled in the art and, therefore, will not be described in detail. The humeral component of the present invention is generally designated 8 and consists of a spherical end 10 having a suitable radius of curvature and sized and shaped to fit into the socket 6. The ball 10 is supported on a shank 12 which terminates in an out-turned circular shoulder 14. Shank 12 is sized and shaped for attaching the humeral component in the medullary canal of the humerus. The shoulder 14 is separated from the ball 10 by a distance approximately equal to the diameter of the ball 10. Thus the shank 12 is substantially longer than the shank of the prior art humeral component shown in FIG. 2. Further, the shoulder 14 is situated at approximately right angles to the major axis of the ball 10 (i.e. the center of contact of the ball and socket) in contrast with the prior art structure wherein the plane of the collar forms an acute angle. However, the biggest distinction is that shoulder 14 is provided with a plurality of holes 16 at its terminal edge. The holes 16 are on the front superior side when implanted in the humerus bone that faces toward the front side thereof and lie in the plane of said superior side. The function of these holes will be later described. This prosthesis requires the removal of the tuberosities 20 of the humerus.

In utilizing the prosthesis of the present invention, the head of the humerus 17 is cut off at substantially right angles to the humerus. This is in contrast to the prior art where one does not excise the tuberosities 20 which frequently impinge on the acromion. The shank 18 is then cemented in known manner into the medullary canal of the humerus 17. One now passes sutures through the holes 16 holding the tendons in place against the bone and in time the tendons fix on the bone.

In FIG. 3 there is shown the method of attaching the subscapularis tendons 26. In a similar manner, the infraspinatus and teres minor tendons are attached at the rear of the humerus, not illustrated.

It is believed apparent from the foregoing that I have provided a novel humeral component for a shoulder prosthesis wherein a relatively long shank is provided on the ball replacing the humeral head and tuberosities and a shoulder is provided at substantially right angles to the center of the ball, said shoulder being provided with a series of holes for the effective attachment of the tendons.

I claim:

1. In a shoulder prosthesis, a humeral component having a superior side when implanted in the humerus bone that faces towards the front side thereof, said humeral component comprising in combination:
   a. a first end terminating in a spherical ball, sized and shaped for fitting in a shoulder socket,
   b. a shoulder offset from said ball by about the diameter of the ball, said shoulder having a superior surface lying in the plane of said superior side and including a disclike edge terminating in a substantially flat surface substantially at a right angle to the principal axis of the ball,
   c. said shoulder having a plurality of holes adjacent said edge on at least said superior surface thereof, whereby sutures can be passed through said holes to enhance fixation of one or more of the tendons of the rotator cuff, namely supraspinatus, subscapularis, infraspinatus and teres minor tendons to bone and
   d. a shaft opposite said first end having a size and shape for attaching said humeral components in the medullary canal of the humerus.